US006010976A

United States Patent [19]
Ryu

[11] Patent Number: 6,010,976
[45] Date of Patent: Jan. 4, 2000

[54] CATALYST FOR MAKING DIALKYL CARBONATES

[75] Inventor: J. Yong Ryu, Pasadena, Tex.

[73] Assignee: Catalytic Distillation Technologies, Pasadena, Tex.

[21] Appl. No.: 09/189,107

[22] Filed: Nov. 10, 1998

Related U.S. Application Data

[62] Division of application No. 09/140,435, Aug. 26, 1998, Pat. No. 5,902,894.

[51] Int. Cl.$^7$ .............................. B01J 31/00; B01J 31/22
[52] U.S. Cl. .......................... 502/156; 502/150; 502/152; 502/172
[58] Field of Search ................................ 502/150, 152, 502/156, 172

[56] References Cited

U.S. PATENT DOCUMENTS

| | | |
|---|---|---|
| 4,327,035 | 4/1982 | Heitz et al. . |
| 4,360,477 | 11/1982 | Hallgreen et al. . |
| 4,435,595 | 3/1984 | Agreda et al. . |
| 4,851,555 | 7/1989 | Weinstein . |
| 4,939,294 | 7/1990 | Agreda et al. . |
| 5,231,212 | 7/1993 | Buysch et al. . |
| 5,534,649 | 7/1996 | Cho et al. . |
| 5,545,600 | 8/1996 | Knudsen et al. ................. 502/152 |
| 5,565,603 | 10/1996 | Saleh et al. . |
| 5,591,883 | 1/1997 | Hwang et al. . |
| 5,759,941 | 6/1998 | Saleh ................................ 502/152 |
| 5,877,336 | 3/1999 | Hergenrother et al. .............. 556/87 |

FOREIGN PATENT DOCUMENTS

| | | |
|---|---|---|
| 0460735A2 | 12/1991 | European Pat. Off. . |
| 0501374B1 | 9/1992 | European Pat. Off. . |
| 0742198A1 | 11/1996 | European Pat. Off. . |
| WO95/17369 | 6/1995 | WIPO . |

OTHER PUBLICATIONS

W.J.Close & M.A.Spielman, "A Proposed Mechanism for the Conversion of Alcohols to Allophanates", Mar. 13, 1953, pp. 4055–4056, vol. 75, Contribution from Abbott Laboratories.

R.Schwalm, P.Ball, H. Fullman & W.Heitz, Urea as a Carbon Dioxide Source in the Synthesis of Carbonates and Polycarbonates and Polycarbonates, pp. 272–273, Federal Republic of Germany, no publication date available.

Luigi Cassar, "Dimethylcarbonate: a new intermediate for a cleaner future",La Chimica & L'Industria, pp. 18–22, Oct. 1989, Italy.

Y.Okada, T.Kondo, S.Asaoka, "Dimethyl Carbonate Production for Fuel Additives", ACS 212th National Meeting, Orlando, Aug. '96, pp. 868–872.

Herbert W. Blohm and Ernest I. Becker, "Allophanates", Chem. Laboratories of the Polytechnic Institute of Brooklyn, New York, Chemical Rev. 1952, 51, pp. 471–504, no month available.

Peter Ball, Heinz Fullman, Reinhold Schwalm & Walter–Heitz, "Synthesis of Carbonates and Polycarbonates by Reaction of Urea with Hydroxy Compounds", C1 Mol. Chem., vol. 1, pp. 95–108, 1984, no month available.

John F. Knifton and Roger G. Duranleau,"Ethylene glycol–dimethyl carbonate cogeneration", Journal of Molecular Catalyst, 1991, pp. 389–399, no month available.

Michael A. Pacheco and Christopher L. Marshall, "Review of Dimethyl Carbonate (DMC) Manufacture and Its Characteristics as a Fuel Additive", Energy & Fuels, 1997, 11, 2–29, no month available.

*Primary Examiner*—Elizabeth D. Wood
*Attorney, Agent, or Firm*—Kenneth H. Johnson

[57] ABSTRACT

A novel catalyst, which is a complex of organotin with a high boiling electron donor compound acting as solvent which includes bidentate ligands which form 1:1 bidentate and/or 1:2 monodentate adducts with $R'_2SnX_2$ (X=Cl, R'O, R'COO or R'COS), $R'_3SnX$, $R'_2SnO$, $Ph_{3-n}R'SnX_n$ or $Ph_{4-n}SnX_n$ (wherein $R'=C_qH_{2q-1}$ n=0, 1 or 2 and q=2 to 12) and mixtures thereof, such as materials having the general formula $RO[CH_2(CH_2)_kCH_2O]_mR$, wherein each R is independently selected from $C_{1-12}$ alkyl, alkaryl or aralkyl moieties, k=0, 1, 2 or 3 and m=1, 2, 3, 4 or 5. The catalyst is useful in the process for producing dialkyl carbonates, such as dimethyl carbonate, from the reaction of a primary alcohol with urea.

15 Claims, 6 Drawing Sheets

CATALYST FOR MAKING DIALKYL CARBONATES

This is a division of application Ser. No. 09/140,435, filed Aug. 26, 1998 and now U.S. Pat. No. 5,902,894.

BACKGROUND OF THE INVENTION

1. Field of the Invention

The present invention relates to a process for the production of dialkyl carbonates, particularly dimethyl carbonate wherein the reaction occurs simultaneously with separation of the reactants and the carbonate products. More particularly the invention relates to a process wherein methanol is reacted with urea and/or alkyl carbamate in the presence of a novel catalyst complex comprising a homogeneous organic tin compound and an electron donor oxygen atom containing compound.

2. Related Art

Dialkyl carbonates are important commercial compounds, the most important of which is dimethyl carbonate (DMC). Dimethyl carbonate is used as a methylating and carbonylating agent. It can also be used as a solvent to replace halogenated solvents such as chlorobenzene. Although the current price of dimethyl carbonate is prohibitively expensive to use as fuel additive, it could be used as an oxygenate in reformulated gasoline and an octane component. Dimethyl carbonate has a much higher oxygen content (53%) than MTBE (methyl tertiary butyl ether) or TAME (tertiary amyl methyl ether), and hence not nearly as much is needed to have the same effect. It has a RON of 130 and is less volatile than either MTBE or TAME. It has a pleasant odor and, unlike ethers, is biodegradable.

In older commercial processes dimethyl carbonate was produced from methanol and phosgene. Because of the extreme toxicity and cost of phosgene, there have been efforts to develop better, non-phosgene based processes.

In one new commercial process, dimethyl carbonate is produced from methanol, carbon monoxide, molecular oxygen and cuprous chloride via oxidative carbonylation in a two step slurry process. Such a process is disclosed in EP 0 460 735 A2. The major shortcomings of the process are the low production rate, high cost for the separation of products and reactants, formation of by-products, high recycle requirements and the need for corrosion resistant reactors and process lines.

Another new process is disclosed in EP 0 742 198 A2 and EP 0 505 374 B1 wherein dimethyl carbonate is produced through formation of methyl nitrite instead of the cupric methoxychloride noted above. The by-products are nitrogen oxides, carbon dioxide, methylformate, etc. Dimethyl carbonate in the product stream from the reactor is separated by solvent extractive distillation using dimethyl oxalate as the solvent to break the azeotropic mixture. Although the chemistry looks simple and the production rate is improved, the process is actually very complicated because of the separation of a number of the materials, balancing materials in various flow sections of the process, complicated process control and dealing with the hazardous chemical, methyl nitrite.

In another commercial process dimethyl carbonate is produced from methanol and carbon dioxide in a two step process. In the fist step cyclic carbonates are produced by reacting epoxides with carbon dioxide as disclosed in U.S. Pat. Nos. 4,786,741; 4,851,555 and 4,400,559. In the second step dimethyl carbonate is produced along with glycol by exchange reaction of cyclic carbonates with methanol. See for example Y. Okada, et al "Dimethyl Carbonate Production for Fuel Additives", ACS, Div. Fuel Chem., Preprint, 41(3), 868, 1996, and John F. Knifton, et al, "Ethylene Glycol-Dimethyl Carbonate Cogeneration", Journal of Molecular Chemistry, vol 67, pp 389–399, 1991. While the process has its advantages, the reaction rate of epoxides with carbon dioxide is slow and requires high pressure. In addition the exchange reaction of the cyclic carbonate with methanol is limited by equilibrium and methanol and dimethyl carbonate form an azeotrope making separation difficult.

It has been known that dialkyl carbonates can be prepared by reacting primary aliphatic alcohols such as methanol with urea in the presence of various heterogeneous and homogeneous catalysts such as dibutyltin dimethoxide, tetraphenyltin, etc. See for example P. Ball et al, "Synthesis of Carbonates and Polycarbonates by Reaction of Urea with Hydroxy Compounds", C1 Mol. Chem., vol 1, pp 95–108, 1984. Ammonia is a by-product and it may be recycled to urea as in the following react on sequence.

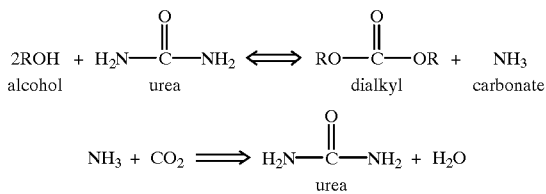

Carbamates are produced at a lower temperature followed by production of dialkyl carbonates at higher temperature with ammonia being produced in both steps.

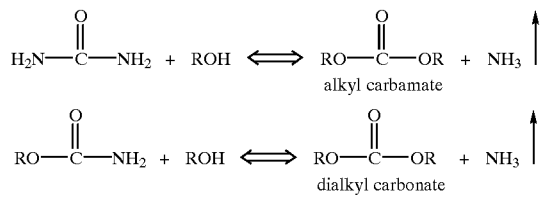

As noted the above two reactions are reversible under reaction conditions. The order of catalytic activity of organotin compounds is $R_4Sn < R_3SnX << R_2SnX_2$, wherein X=Cl, RO, RCOO, RCOS. A maximum reaction rate and minimum formation of by-products are reported for dialkyl tin (IV) compounds. For most catalysts (Lewis acids), higher catalyst activity is claimed if the reaction is carried out in the present of an appropriate cocatalyst (Lewis base). For example, the preferred cocatalyst for organic tin (IV) catalysts such as dibutyltin dimethoxide, dibutyltin oxide, etc. are triphenylphosphine and 4-dimethylaminopyridine. However, the thermal decomposition of intermediate carbamates to isocyanic acid (HNCO) or isocyanuric acid ((HNCO)$_3$) and alcohols is also facilitated by the organotin compounds such as dibutyltin dimethoxide or dibutyltin oxide employed in the synthesis of aliphatic carbamates. WO 95/17369 discloses a process for producing dialkyl carbonate such as dimethyl carbonate in two steps from alcohols and urea, utilizing the chemistry and catalysts published by P. Ball et al. In the first step, alcohol is reacted with urea to produce an alkyl carbamate. In the second step, dialkyl carbonate is produced by reacting further the alkyl carbamate with alcohol at temperatures higher than the first step. The reactions are carried out by employing an autoclave reactor. However, when methanol is reacted with methyl carbamate or urea, N-alkyl by-products such as N-methyl methyl carbamate (N-MMC) and N-alkyl urea are also produced. The dialkyl carbonate is present in the reactor in an amount between 1 to 3 weight % based on total carbamate and alcohol content of the reactor solution.

SUMMARY OF THE INVENTION

Dialkyl carbonates are prepared by reacting alcohols with urea or alkyl carbamate or both in the presence of a organic Group IVA (IV) complex such as a dibutyltin dimethoxide complex wherein the reaction is preferably carried out in the reboiler of a distillation still with concurrent distillation of the dialkyl carbonate.

In a preferred embodiment the complexing agents are high boiling organic electron donor compounds which have one, two, three, four or more oxygen atoms per molecule, preferably two or more oxygen atoms per molecule preferably polyglycol ethers such as triglyme (triethylene glycol dimethyl ether), whose boiling point is preferably higher than either methanol or dimethyl carbonate and which serve as both cocatalysts and solvent. Thus, the present invention provides an improved process by concurrently distilling dialkyl carbonate away from the reaction concurrently with the reaction and by preferably using specific complexing agents for the organotin catalyst.

The preferred electron donor oxygen atom containing compounds useful as cocatalyst and/or solvent comprises bidentate ligands which form 1:1 bidentate and/or 1:2 monodentate adducts with $R'_2SnX_2$ (X=Cl, R'O, R'COO or R'COS), $R'_3SnX$, $R'_2SnO$, $Ph_{3-n}R'SnX_n$ or $Ph_{4-n}SnX_n$ (wherein $R'=C_qH_{2q-1}$ n=0, 1 or 2 and q=2 to 12) and mixtures thereof, such as materials having the general formula $RO[CH_2(CH_2)_kCH_2O]_mR$, wherein each R is independently selected from $C_{1-12}$ alkyl, alkaryl or aralkyl moieties, k=0, 1, 2 or 3 and m=1, 2, 3, 4 or 5. In addition these materials may be admixed with higher hydrocarbons, preferably having 8 to 12 carbon atoms, such as dodecane and xylenes.

Examples of ligands which form 1:1 bidentate and/or 1:2 monodentate adducts with $R'_2SnX_2$ include diethylene glycol ether, 1,3-dimethoxy propane, 1,2-dimethoxypropane, dipropylene glycol dimethyl ether, 1,4-dioxane, di-n-butyl ether and the like.

One advantage of producing dimethyl carbonate from urea and methanol is in the separation of dimethyl carbonate from the reaction mixture. Since water is not coproduced, the reaction mixture (the overhead product) does not form a ternary azeotrope and, hence the separation of the product dimethyl carbonate form the overhead mixture is easier than the current commercial processes which have to deal with such a ternary azeotrope.

DETAILED DESCRIPTION OF THE PREFERRED EMBODIMENT

Figure 1:
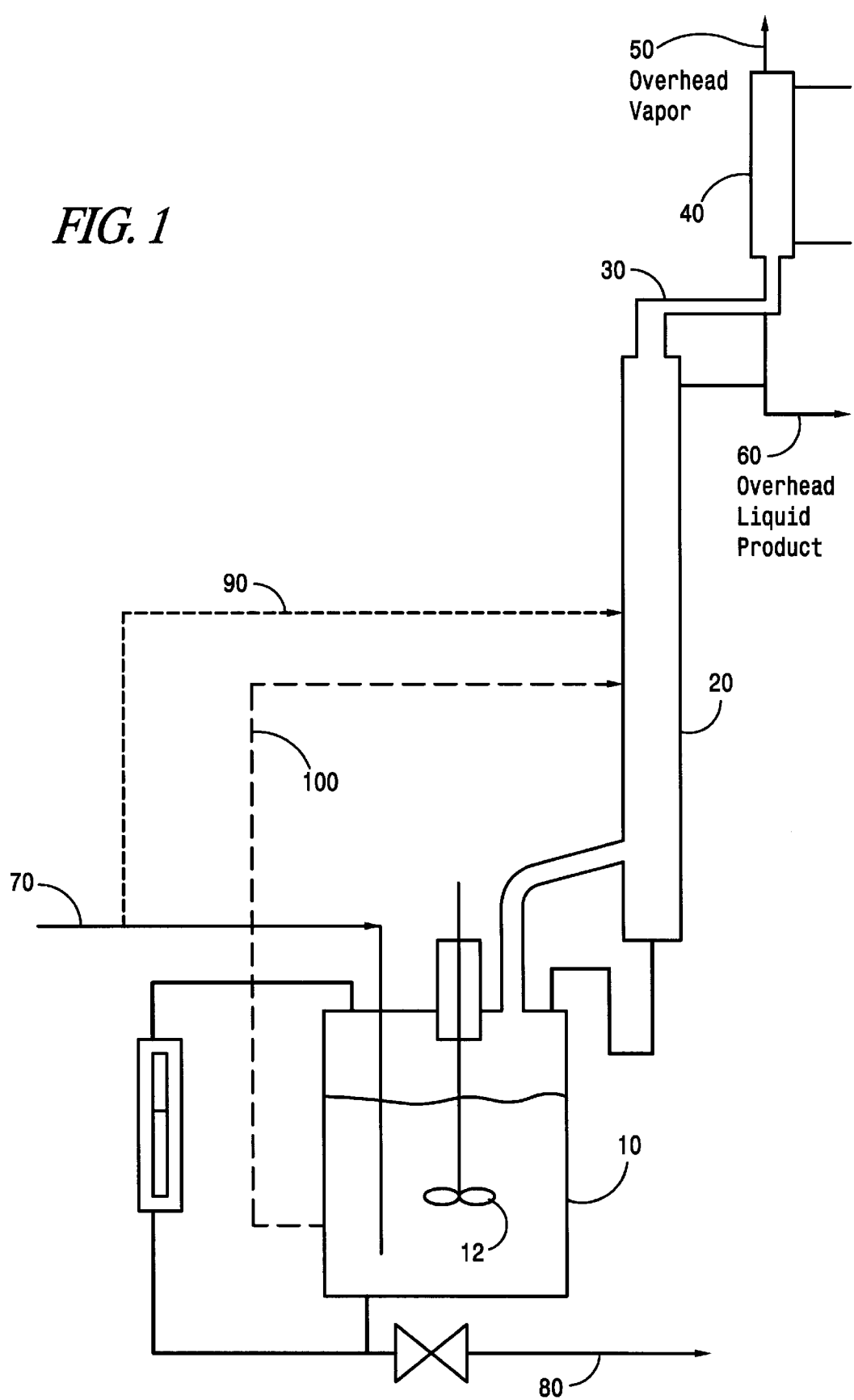
FIG. 1 is a schematic of an apparatus that can be employed to carry out the present invention.

The reaction is preferably carried out in the presence of a high boiling electron donor oxygen containing solvent, which also serves as the complexing agent with the organotin compound, by employing the reboiler of distillation still as the reactor. The reactor temperature is controlled by changing the overhead pressure of the distillation column. The use of the reboiler and distillation column allows effective removal of the reaction products, dimethyl carbonate and ammonia, while keeping the homogeneous catalyst and solvent in the reactor. The column may be of any conventional form such as trays, packing, or combinations thereof.

The novel organotin catalyst complex may be prepared by mixing organotin compound with high boiling electron donor oxygen containing compounds, such as ethers, usually at room temperature, in situ in the reaction zone, e.g. the reboiler at the initiation of the dialkyl carbonate reaction. When organotin halides, acetates or oxides are used as the catalyst precursors, the complex formation may be carried out prior to the initiation of the dialkyl carbonate, in order to remove the acid or water, which is generated in the complexing reaction, although it is not necessary or preferably to do so, since the acidic component and water are easily remove overhead during the startup of the dialkyl carbonate reaction.

The reaction order of 2-methylhexyl carbamate in the presence of excess 2-ethylhexyl alcohol has been proposed to be pseudo first order, or less than one. Therefore a lower methanol concentration relative to a given concentration of methyl carbamate is expected to be favorable for higher conversion rate of methyl carbamate. The use of both the reboiler-distillation column, and the high boiling oxygen atom(s) containing solvent such as diglyme (diethylene glycol dimethyl ether), triglyme (triethylene glycol dimethyl ether) or tetraglyme (tetraethylene glycol dimethyl ether), etc, allows carrying out the reaction under any desired pressure while maintaining any desired concentration of reactants (methanol, urea and carbamate) and product (dimethyl carbonate) in the reaction zone to obtain the best economical result.

In choosing the high boiling ethereal solvent the dialkyl carbonate produced in the reaction is a consideration. For example triethylene dimethyl ether is preferred for the production of dimethyl carbonate, but it is not preferred for the production of diethyl carbonate, because the product is contaminated with methyl ethyl carbonate and the solvent is slowly converted to triethylene diethyl ether. A preferable solvent for diethyl carbonate production would be tri- or tetraethylene glycol diethyl ether.

In the present invention the desired ratio of the solvent to methanol in the reaction medium is controlled by changing the ratio of methanol to high boiling electron solvent at a given concentration of carbamate or a given combined concentration of urea and carbamate in the reboiler. The use of the high boiling electron donor solvent such as triglyme as a cocatalyst as well as a part of the reaction medium overcomes the shortcomings of the earlier processes.

Despite the high yield or selectivity of carbonates claimed in WO 95/17369 and P. Ball et al ($C_1$ Mol. Chem., 1, 95, 1984 and ACS, Div. of Polymer Chemistry, Polymer Preprints, 25, 272, 1984 and $C_1$ Mol. Chem., 1984, Vol. 1, pp.95–108) it is important to understand the decomposition of urea and carbamate. Urea can decompose thermally or catalytically to isocyanic acid and ammonium isocyanate or biuret ($N_2NCONHCONH_2$) under the reaction conditions employed to prepare dialkyl carbonates (D. J. Belson et al., Chemical Soc. Reviews, 11, 41–56, 1982). Analysis of the overhead vent gas taken during the reaction indicates some carbon dioxide produced. Although P. Ball et al stated that aliphatic carbamates can be distilled without decomposition, carbamates also can decompose thermally or catalytically to isocyanic or isocyanuric aid and alcohol (J. J. Godfrey, U.S. Pat. No. 3,314,754), or form allophanates (ROCONHCONH$_2$) H. W. Blohm and E. I. Becker, Chem. Rev., 1952, 51, 471). Ball et al stated that the thermal decomposition of the carbamates into isocyanic acid and alcohol competes with the formation of carbonate. However, the paper claims that this decomposition does not occur in the presence of suitable cocatalysts for some catalysts. Triphenylphosphine and 4-dimethylaminopyridine are cited as good cocatalysts for organotin catalysts. Present EXAMPLES 4A and 4B indicate that methyl carbamate decomposes thermally or catalytically in the presence of organotin catalysts.

Dimethyl carbonate is a highly active compound so in order to improve the selectivity to dimethyl carbonate, the concentration of dimethyl carbonate in the reboiler should be kept as low as possible. In the present invention a very low concentration of dimethyl carbonate is obtained by selecting the proper high boiling solvent and controlling the overhead pressure which is a function of the ratio of methanol to high boiling electron donor solvent in the reboiler at a given concentration of methyl carbamate or given combination of methyl carbamate and urea. The use of the high boiling electron donor compounds as both cocatalyst and solvent improves the rate of forming dialkyl carbonates (because of effective removal of both ammonia and dimethyl carbonate from the reaction zone) and, at the same time, prevents the formation of by-products such as N-alkyl alkyl carbamate, alkyl amine, and N-alkyl urea or decomposition of urea or carbamate at relatively high concentration of dialkyl carbonate in both reactor and overhead products. High concentration of dialkyl carbonate in the overhead product reduces the cost of separating the dialkyl carbonate from methanol for recycle.

Since the reaction can be carried out at lower pressures (less than 100 psig) the new process has a number of advantages; lower cost for the material of construction, low catalyst inventory cost, easier removal of the ammonia and dimethyl carbonate products, and ease of control of the optimum concentration of methanol in the reactor for the maximum dimethyl carbonate formation rate and selectively to dimethyl carbonate.

Flushing out the reactor (reboiler) with an inert gas such as nitrogen although not necessary, be included as as part of the startup. If inert gas is used to flush the reboiler the lower pressures preferably used in the present reaction system allows for the use of a blower instead of a compressor for the inert gas.

The preferred range of reactor temperature is from 270 to 400° F., preferably from 300–380° F. The preferred overhead pressure is within the range of 10–250 psig, more preferable between 20–200 psig and most preferably between 25–150 psig. The desirable weight ratio of high boiling electron donor solvent to methanol in the reactor is from 100–0.01:1, preferably 5–0.1:1. The preferred concentration of organotin compounds in the reactor is from 0.5 to 40 wt. %, preferably from 2–30 wt. % based on the total content in the reactor. The preferred overhead product rate is controlled to have from 4–35 percent by weight dimethyl carbonate, preferably form 5–25 wt. %. The preferred concentration of methyl carbamate or combined concentration of methyl carbamate and urea in the reactor is from 5–60 wt. %, preferably from 15–55 wt. % during continuous operation.

For the continuous production of dimethyl carbonate, the urea solution may be directly pumped into the reactor or partially or completely converted to methyl carbamate prior to pumping into the reactor. Such conversion could be accomplished in a feed preheater or in separate reactor. The solvent for the urea solution can be substantially pure methanol or very dilute dimethyl carbonate solution in methanol. An example of the dilute dimethyl carbonate solution (about 2% dimethyl carbonate in methanol) is the overhead recycle stream from a dimethyl carbonate recovery column. In one embodiment all or a portion of the urea solution may be fed to the distillation column instead of the reboiler to partially convert urea to methyl carbamate prior to entering the reboiler. In another embodiment material from the reboiler may be added to the distillation column with the urea feed steam or at some other point along the column.

Referring now to FIG. 1 is a schematic representation of the experimental apparatus used for the following examples is shown. The 350 ml reboiler 10 of the still equipped with a stirring blade 12 was used as the reactor. The ¾" diameter distillation column 20 was packed with ⅛" ceramic saddles. Reactants, solvent and catalyst were charged to the reboiler 10 at ambient temperature (~75° F.). The reactions were carried out by raising the reboiler temperature to a selected temperature by controlling the overhead pressure of the column. During the reaction the reactants were pumped into the reboiler continuously. The reaction products were removed from the reboiler as overhead product from the column 20 via flow line 30 and condensed in condenser 40 where the ammonia was removed as vapor via flow line 50 and product dimethyl carbonate removed via flow line 60. During the reaction, the liquid volume in the reboiler was maintained at a preferred constant level by pumping in additional methanol, methanol-solvent mixture or the solutions of urea or methyl carbamate in methanol or methanol-solvent mixture through flow line 70. As an option a portion of the urea can be fed directly to the distillation column via flow line 90 as shown. In a similar manner catalyst complex from reboiler 10 may be fed directly to the distillation column via flow line 100. Samples for analysis were removed from the reboiler via flow line 80. Samples from the overheads (total overheads) and bottoms were analyzed by gas chromatograph. The reboiler temperature was controlled by controlling the overhead pressure. To raise the temperature the overhead pressure was raised. When the high boiling oxygen atom containing solvent was used, the novel organotin complex catalyst was formed by mixing dibutyltin dimethoxide and the solvent such as triglyme together in the reboiler. The reaction system in the reactor may be characterized as homogeneous.

EXAMPLE 1A

Figure 2:
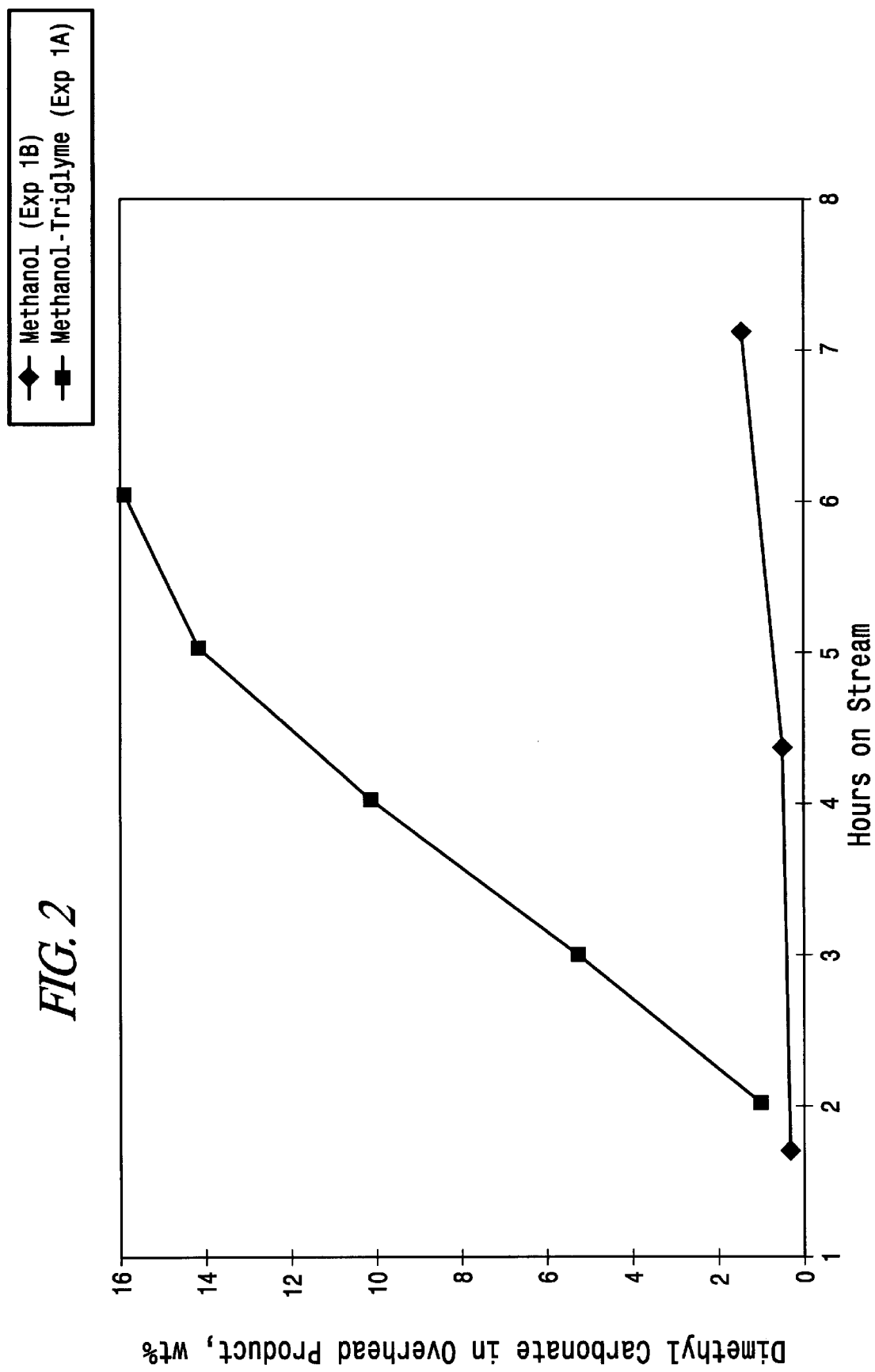
FIG. 2 is a plot of dimethyl carbonate in overhead versus hours on stream comparing methanol only with methanol+ triglyme.

The reboiler of the distillation still was charged with 96 g of urea, 112 g of methanol, 113 g of triglyme (triethylene glycol dimethyl ether) and 25.5 g catalyst (dibutyltin dimethoxide) in the reboiler and then raising the reboiler temperature to the desired temperature with stirring. During the heating and reaction, 5 weight percent triglyme solution in methanol was continuously pumped into the reboiler to maintain constant liquid level in the reboiler. The reboiler temperatures during the reaction were maintained by controlling overhead pressure. When the reboiler temperature reached the desired temperature (320° F.), the withdrawal of the overhead liquid product was started at the 1 cc/m rate through the line 60. At the beginning of the reaction, the reboiler temperature was maintained at 320° F. for an hour and then at 355° F. until shut-down. The overhead pressures at 320° F. and 355° F. at the beginning were 100.6 and 106.5 psig, respectively. The column temperatures were 325° F. at the bottom section of the column and 253° F. at the top section of column at 355° F. reboiler temperature at the beginning of the reaction. The overhead pressure was lowered as the conversion of urea to methyl carbamate progressed. At the end (6 hours on stream) of the run, the overhead pressure was 68.1 psig. The column temperature was 295° F. at the bottom section of column and 234° F. at the top section of the column. The overhead liquid products were composed of methanol and dimethyl carbonate with small amount of dissolved ammonia. No triglyme was observed in the overhead products. The change of the composition of the overhead liquid products during the run are illustrated in FIG. 2. While the bottom product sample taken at the end of the 6 hour run contained 7.2% dimethyl carbonate and 22.6% methyl carbamate, the overhead product contained 16.0% dimethyl carbonate. The content of urea in the bottoms product sample was unknown because urea could not be analyzed by gas chromatography due to decomposition of urea.

EXAMPLE 1B

The reaction was carried out in the identical manner to EXAMPLE 1A without the cocatalyst. The reboiler was charged with 96 g of urea, 200 g of methanol and 50.1 g of dimethyltin dimethoxide. The reboiler temperatures during the reaction were maintained by controlling overhead pressure. The flow rate of the overhead liquid product was 1 cc/min. To maintain a constant liquid level in the reboiler during the run, pure methanol was pumped into the reboiler. At the beginning of the reaction, the reboiler temperature was maintained at 320° F. for an hour and then at 365° F. until shut-down. The overhead pressures at 320° F. and 365° F. at the beginning were 163 and 261 psig. The column temperature was 342° F. at the bottom section of the column and 325° F. at the top section of the column at the beginning of 365° F. reboiler temperature. The pressure was raised as the reaction progresses to maintain 365° F. reboiler temperature. At the end (7.1 hours on stream) of run, the overhead pressure was 357 psig. The column temperature was 362° F. at the bottom section of the column and 353° F. at the top section of the column. The change of the composition of the overhead liquid products during the run are illustrated in FIG. 2. While the bottom product sample taken at the end of 7.1 hour run contained 7.8% dimethyl carbonate and 2.2% methyl carbamate, the overhead product contained only 1.5 dimethyl carbonate. The content of urea in the bottoms product sample was unknown because urea could not be analyzed by gas chromatography due to decomposition of urea.

EXAMPLE 1A demonstrates how effectively the product carbonate is removed from the reaction zone in the present invention as shown in FIG. 2. When the reaction is carried out according to the preferred embodiment of the present invention starting from urea, the product dimethyl carbonate content in the overhead increases rapidly as urea is converted to methyl carbamate which in turn is converted to dimethyl carbonate. Because of relatively low pressure of the still, the product dimethyl carbonate is effectively removed as overhead product from the reboiler as indicated by the concentration of dimethyl carbonate in the overhead and bottom products at the end of run; more dimethyl carbonate (16%) in the overhead product than in the bottom product (7.2%). The sample taken from the reboiler contained 22.6% methyl carbamate. Urea is effectively converted to dimethyl carbonate with little indication of decomposition of urea and methyl carbamate. When the reaction is carried out without triglyme as in Example 1B, less product dimethyl carbonate is removed as the overhead product as shown in FIG. 2. Dimethyl carbonate is accumulated in the reboiler by effective rectification of the column under higher pressure rather than removed as the overhead mixture. The overhead product at the end of run contains only 1.5% dimethyl carbonate which compares with 7.8% dimethyl carbonate in the bottom product. Undesired side reactions of product dimethyl carbonate and the decomposition of urea and carbamate occur because of the accumulation of DMC in the reboiler and absence of cocatalyst such that at the end of run, there are only 2.2% methyl carbamate and 7.8% dimethyl carbonate in the reboiler.

EXAMPLE 2

Catalyst Complex

When dibutyltin dimethoxide (liquid at room temperature) was mixed together with methanol, ethyl ether or toluene, dibutyltin dimethoxide catalyst was completely soluble in these solvents and detectable by gas chromatography if analyzed the solutions by using TCD detector and DB-5 gas chromatography column. Dibutyltin dimethoxide in methanolic solution or toluene was detectable (5.38 minutes retention time) by gas chromatography. The analysis of the dibutyltin dimethoxide solution in diethyl ether indicated that the organotin compound in the solution was no longer dibutyltin dimethoxide. The tin compound in the solution was much heavier than dibutyltin dimethoxide so that the peak for the new organotin complex compound in the ether solution has about 3 time longer retention time (15.68 min.). When dibutyltin dimethoxide was mixed with mixtures of triglyme and methanol or pure triglyme ($CH_3OCH_2CH_2OCH_2CH_2OCH_2CH_2OCH_3$) at room temperature, white fluffy precipitate was formed which slowly saddled down at the bottom of bottles. If the white precipitate suspended solution was filtered immediately and the clear filtrate was analyzed with gas chromatography the organotin compound was still detectable, although the concentration was lower than expected. With low concentration (10 weight %) of the organotin catalyst in the mixed solution, the white precipitate dissolved completely to become clear solution by standing at room temperature overnight. If the white precipitate suspended solution was warmed, the white precipitate immediately became soluble. When these clear solutions were analyzed with gas chromatography, the dimethyltin dimethoxide was no longer detectable.

EXAMPLE 2 demonstrates the formation of adduct complex compounds by the reaction of dibutyltin dimethoxide ($Bu_2Sn(IV)(OCH_3)_2$) with the electron donor etherial compounds. In the present invention, the complex compounds are employed as catalysts which are the adducts of the electron donor oxygen atom(s) containing molecules to the organotin compounds. The catalytic complex compound was prepared by simply mixing dibutyltin dimethoxide and triglyme or other electron donor etherial compounds together in the reboiler of the distillation still.

EXAMPLE 3A

Figure 3:
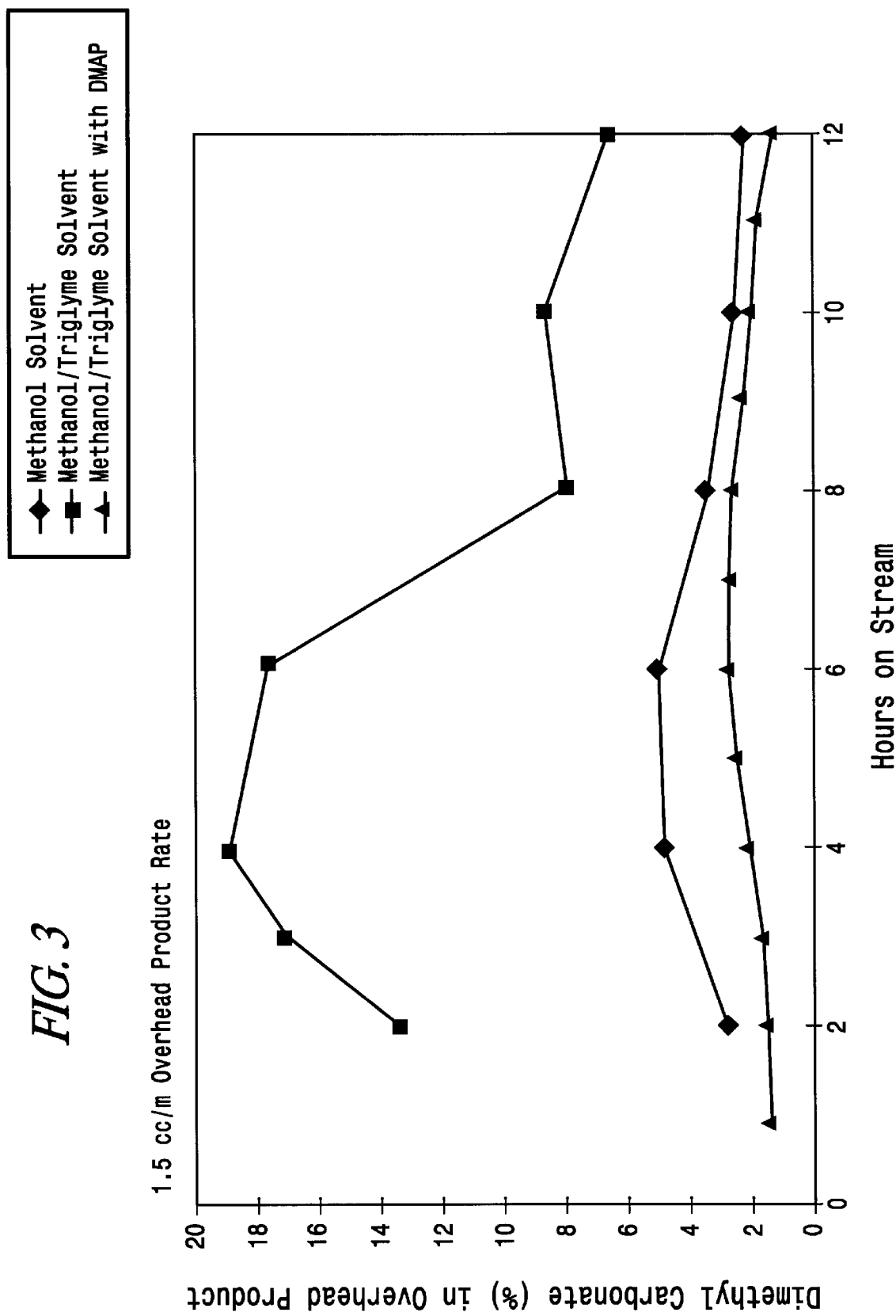
FIG. 3 is a plot of dimethyl carbonate in overhead versus hours on stream comparing methanol only with methanol+ triglyme and methanol+triglyme+DMAP at a 1.5 cc/min overhead rate.
Figure 4:
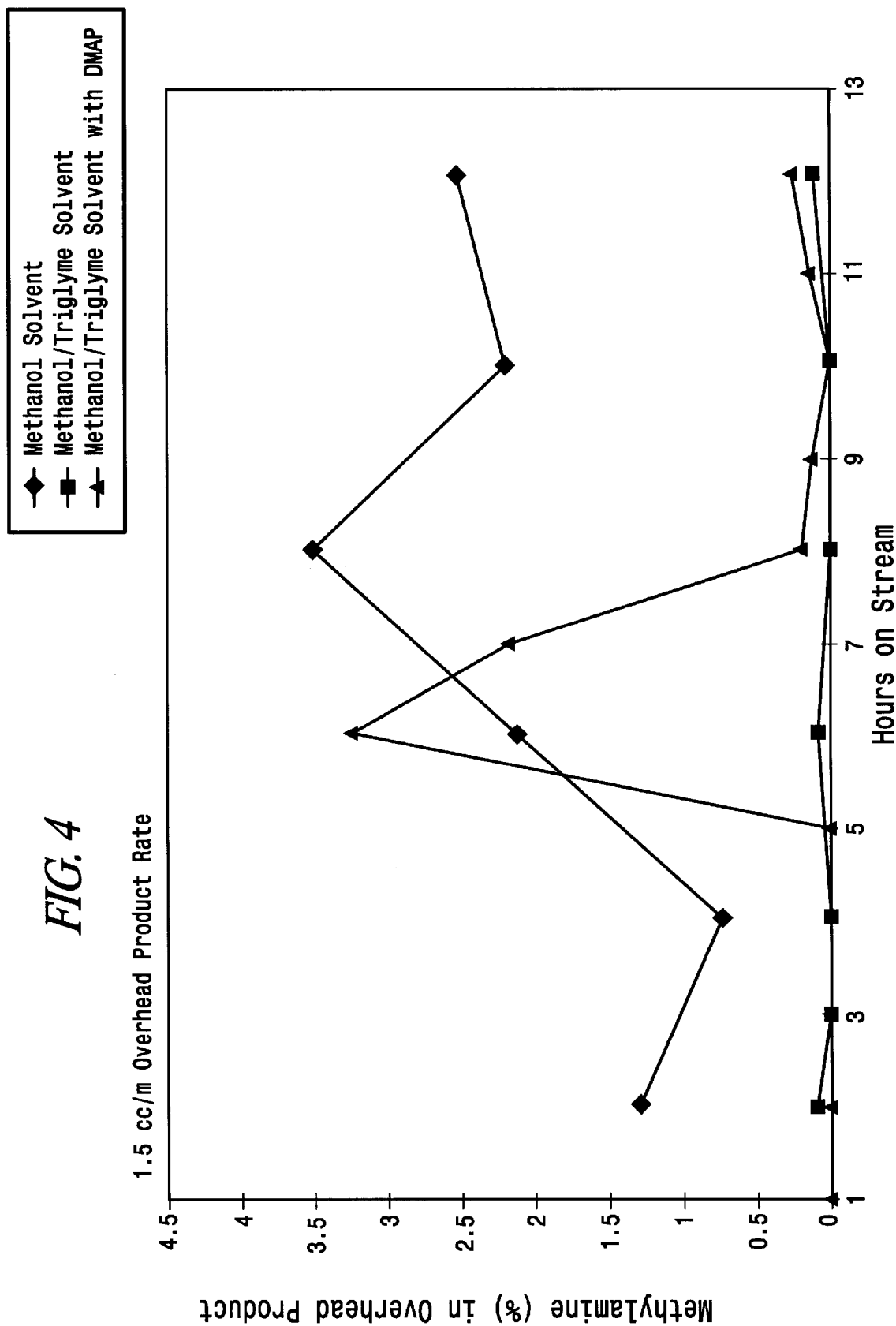
FIG. 4 is a plot of methylamine in overhead versus hours on stream comparing methanol only with methanol+ triglyme and methanol+triglyme+DMAP at a 1.5 cc/min overhead rate.

The reboiler of the distillation still was charged with 125 g methyl carbamate, 100 g methanol, 100 g triglyme and 24.7 g dibutyltin dimethoxide. The reboiler temperature was maintained at 355–363° F. by controlling the overhead pressure. The flow rate of the overhead liquid product was set at 1.5 cc/min. To maintain a constant liquid level in the reboiler, a mixture of methanol and triglyme prepared by mixing 1650 g methanol with 142.5 g triglyme was continuously pumped into the reboiler. The reaction was carried out for 6 hours each day for 2 days, for a total of 12 hours. After a 6 hour run, the unit was shut down. On the following day the unit was restarted. During the reaction the overhead liquid products were collected into a reservoir. At the end of the run all the composite overhead liquid product in the reservoir and the inventory materials in the reboiler and column were removed from the system and weighted and then analyzed. During the run the samples taken from the unit for analysis were weighted. The result of this experiment is listed in Table 1. The change in the compositions of dimethyl carbonate and methylamine in the overhead liquid products during the run are illustrated in FIG. 3 and 4 respectively. The overhead pressures at 355° F. at the beginning and the end were 53.4 psig and 139 psig, respectively. The column temperatures at the bottom and top section of the column were 234° F. and 200° F. at the beginning, and 288° F. and 277° F. at the end of 12 hours run. The analysis of the bottom product sample taken from the reboiler at the end of 12 hours run indicated 0.1% ammonia, 4.1% dimethyl carbonate, 0.3% N-MMC, 2.7% methyl carbamate, 32.6% methanol, and 60.2 triglyme. The overhead product contained 6.9% dimethyl carbonate. The content of urea in the bottom product sample was unknown, because urea could not be analyzed by gas chromatography due to decomposition of urea.

The EXAMPLE 3A demonstrates the superior yield and selectivity for dimethyl carbonate of the present invention compared with the prior art. The dimethyl carbonate content in the overhead liquid product of the present invention was at least 3 times higher than the dibutyltin dimethoxide alone (Example 3B). Consequently the separation of dimethyl carbonate from the overhead product can be achieved at much lower cost and much reduced amount of material recycle. When only methanol is used as the solvent (Example 3B), the increase of the overhead liquid product rate slowly improves the selectivity of dimethyl carbonate and reduces the formation of undesired by-products such as N-MMC (N-methyl methyl carbamate) and methylamine, however, the amount of the undesired by-products are still about 10 times higher than the preferred embodiment of in the present invention. The increase of the overhead product rate with the cocatalyst has little effect on the dimethyl carbonate selectivity. The increase of the overhead rate simply dilutes the concentration of dimethyl carbonate in the overhead product stream. The overhead products from the present invention generally contain no methylamine or at most trace amounts.

EXAMPLE 3B

The reaction was carried out by utilizing the distillation still. The run was carried out in the identical manner to the EXAMPLE 3A but without the cocatalyst. The reboiler was charged with 125 g methyl carbamate, 200 g methanol and 25.3 g dibutyltin dimethoxide. The flow rate of the overhead product was set at 1.5 cc/m. Methanol was continuously pumped into the reboiler to maintain a constant liquid level in the reboiler. The result is listed in Table 1. The change in the compositions of dimethyl carbonate and methylamine in the overhead liquid products during the run are illustrated in FIG. 3 and 4, respectively. The overhead pressures at 355° F. at the beginning and the end were 268.4 and 374.4 psig respectively. The column temperatures at the bottom and top section of the column were 332° F. and 321° F. at the beginning, and 353° F. and 348° F. at the end of 12 hours run. The analysis of the bottom product sample taken from the reboiler at the end of 12 hours indicated trace ammonia, 6.9% dimethyl carbonate, 3.6% N-MMC, 2.1% methyl carbamate, 86.6 methanol, and 0.7% others. The overhead product contained 2.1% dimethyl carbonate and 2.5% methylamine. The content of urea in the bottom product sample was unknown because urea could not be analyzed by gas chromatography due to urea decomposition.

EXAMPLE 3C

Triglyme was used as solvent to distill off the dimethyl carbonate product from the reaction zone, and the reaction was carried out by utilizing the distillation still. The experiment was carried out in the identical manner to the EXAMPLE 3A. The reboiler was charged with 125 g methyl carbamate, 100 g methanol, 21 g 4-dimethylaminopyridine (DMAP) cocatalyst, 79 g triglyme and 24.4 g dibutyltin dimethoxide. The run was continued for 12 hours without interruption. To maintain a constant liquid level in the reboiler, a mixture of methanol and triglyme prepared by mixing 1650 g methanol with 142.5 g triglyme was continuously pumped into the reboiler. The result is listed in the Table 1. The change in the compositions of dimethyl carbonate and methylamine in the overhead liquid products during the run are illustrated in FIG. 3 and 4, respectively. The reboiler temperature was maintained at 344–357° F. by controlling the overhead pressure. The overhead pressures at 355° F. at the beginning and the end were 58.9 and 81 psg, respectively. The column temperatures at the bottom and top section of the column were 238° F. and 226° F. at the beginning and 256° F. and 245° F. at the end of 12 hours run respectively. The analysis of the bottom product sample taken from the reboiler at the end of 12 hours run indicated 0.2 dimethyl carbonate, 4.2% N-MMC, 0.5 methyl carbamate, 18.5% methanol, 7.0% 4-dimethylaminopyridine, 69.3% triglyme and 0.3% others. The overhead product contained 1.4% dimethyl carbonate and 0.2 methylamine. The concentration of urea in the bottom product sample was unknown but expected to be very low.

TABLE 1

| | Example | | |
|---|---|---|---|
| Solvent | 3A<br>100 MeOH-<br>100 TG | 3B<br>200 MeOH | 3C<br>100 MeOH-<br>79TG-21DMAP |
| Reboiler Temp, ° F. | 355 | 355 | 355 |
| Ovhd P, psig | | | |
| initial | 53.4 | 268.4 | 58.9 |
| final | 139 | 374.4 | 81 |
| Rate, cc/min | 1.5 | 1.5 | 1.5 |
| Mass Balance, % | 103.1 | 105.7 | 89.9 |

TABLE 1-continued

| Solvent | Example | | |
|---|---|---|---|
| | 3A<br>100 MeOH-<br>100 TG | 3B<br>200 MeOH | 3C<br>100 MeOH-<br>79TG-21DMAP |
| Mole Balance*, % | 94.0 | 41.0 | 17.4 |
| Apparant MC conv., m % | 95.9 | 93.2 | 98.9 |
| Apparent Selectivities*, m % | | | |
| DMC | 90.2 | 31.8 | 9.7 |
| N-MMC | 0.6 | 8.9 | 6.8 |
| DMC removed as ovhd product, g | 99.2 | 23.2 | 13.6 |

*The urea content in the reboiler was not included in the calculation.
TG; triglyme
DMAP; 4-dimethylaminopyridine In EXAMPLE 3C, 4-dimethylaminopyridine (DMAP) was used as cocatalyst as disclosed in the Cl Mol. Chem., 1984, Vol 1, 95–108, Ball et al, "Synthesis of Carbonates and Polycarbonates by Reactions of Urea with Hydroxy Compound". In addition triglyme also was used to carry out the reaction under low pressure according to the present invention. Since DMAP is much stronger Lewis base than triglyme the effect of triglyme on the catalyst as cocatalyst is minimal. As shown in Table 1 and FIG. 3, the organotin complex compound catalyst, which is adduct complex $(BU_2Sn[OCH_3]_2.xDMAP$, wherein x=1 or 2 or both), has very poor selectivity for dimethyl carbonate. The analyses of the overhead vapor samples taken during the run confirmed the decomposition of methyl carbamate, because the gas samples contained very large volumes of carbon dioxide. In EXAMPLE 3C the analyses of the overhead liquid product and the bottom product taken at the end of 12 hours indicate that dimethyl carbonate was effectively removed from the reaction zone because the composition of dimethyl carbonate in the overhead product was 7 times higher than that of the bottom product. The formation of undesired by-product (N-MMC and methylamine) was much higher than EXAMPLE 3A, but somewhat better than the EXAMPLE 3B, probably due to effective removal of dimethyl carbonate and ammonia during the run.

EXAMPLE 4A

Comparison

The thermal decomposition of methyl carbamate was carried out. A methyl carbamate (12.3 weight percent) solution was prepared by dissolving 35 g methyl carbamate in 250 g triglyme in a 350 ml round bottom flask which was equipped with reflux column. The solution was refluxed with stirring at 338 to 356° F. After 12.45 hours reaction, the solution contained 8.2% methyl carbamate and 0.9% methanol, indicating thermal decomposition of methyl carbamate. The color of solution changed from water clear at the beginning to clear golden yellow solution, indicating formation of heavier compounds, and very small amount of white solid was deposited at the bottom of condenser.

EXAMPLE 4B

Comparison

The catalytic decomposition of methyl carbamate was carried out by using the same equipment set-up in the EXAMPLE 4A. A methyl carbamate (11.9 weight percent) solution in triglyme was prepared by dissolving 35 g methyl carbamate in 250 g triglyme and then adding log dibutyltin dimethoxide to the solution. After 4 hours reaction at 313 to 320° F., the solution contained 7.6 weight percent methyl carbamate, 1.4 weight percent methanol and only 0.8 weight percent dimethyl carbonate, indicating the faster decomposition rate catalyzed by dibutyltin dimethoxide-triglyme complex. The color of the solution changed from water clear at the beginning to clear orange and some white solid was deposited at the bottom of condenser indicating again formation of heavier materials which could not be detected with gas chromatography. After 12 hours reaction the solution contained only 2.7 weight percent methyl carbamate, 1.2 weight percent methanol, and 2.7% dimethyl carbonate. Visual examination indicated that the amount of white solid material deposited at the bottom of reflux column was increased slightly compared with the EXAMPLE 4A.

EXAMPLE 5A

The experiment was carried out in the same manner in the EXAMPLE 3A. The reboiler of the distillation still was charged with 125 g methyl carbamate, 100 g methanol, 100 g triglyme and 25.0 g dibutyltin dimethoxide. The reboiler temperature was maintained at 352–356° F. by controlling the overhead pressure during the reaction. The flow rate of the overhead liquid product was set at 2.5 cc/min. A methyl carbamate solution prepared by dissolving 120 g methyl carbamate in a mixed solution of 1960 g methanol and 40 g triglyme was pumped into the reboiler to maintain the constant liquid level in the reboiler. The reaction was terminated after 12 hours on stream. The result of this experiment is listed in Table 2. The overhead pressures at the beginning and the end were 39.4 psig and 123.9 psig, respectively. The column temperatures at the bottom and top section of the column were 224 and 211° F. at the beginning, and 283 and 272° F. at the end of 12 hours run. The analysis of the sample taken from the reboiler at the end of run indicates 0.2% ammonia, 14.8% methanol, 3.3% dimethyl carbonate, 22.4% methyl carbamate, 58.4% triglyme and 0.9% N-MMC. The overhead product contained 9.0% dimethyl carbonate. The content of urea in the bottom product sample was unknown because urea could not be analyzed by gas chromatography due to urea decomposition.

EXAMPLE 5B

The experiment was carried out in the identical manner to the EXAMPLE 5A but without the cocatalyst. The reboiler was charged with 125 g methyl carbamate, 200 g methanol and 24.6 g dibutyltin dimethoxide. The reboiler temperature was maintained at 352–356° F. by controlling the overhead pressure during the reaction. The flow rate of the overhead liquid product was set at 2.5 cc/min. A methyl carbamate solution prepared by dissolving 125 g methyl carbamate in 2000 g methanol was pumped into the reboiler to maintain the constant liquid level in the reboiler. The reaction was terminated after 12 hours on stream. The overhead pressures at the beginning and the end were 207.7 and 299.5 psig respectively. The column temperatures at the bottom and top section of the column were 317° F. and 305° F. at the beginning, and 342° F. and 331° F. at the end of 12 hours run respectively. The analysis of the sample taken from the reboiler at the end of run indicated 0.4% ammonia, 60.8% methanol, 6.7% dimethyl carbonate, 27.6% methyl carbamate, 4.2% N-MMC and 0.2% unknown. The overhead product contained 4.7% dimethyl carbonate and 0.1% methylamine. The result is listed in the Table 2. The content of urea in the bottom product sample was unknown because urea could not be analyzed by gas chromatography due to urea decomposition.

EXAMPLES 4A and 4B indicate slow thermal decomposition of methyl carbamate and that the organotin compounds can be effective catalysts for the decomposition of methyl carbamate and urea in the absence of methanol. Too low a concentration of methanol in the reaction medium can promote the decomposition of methyl carbamate or urea or both. Too high concentration of methanol will slow down the reaction rate and cause high reactor pressure which will cause difficulty in distilling off dimethyl carbonate from the reboiler resulting in higher by-product formation. Therefore, it is important to maintain an optimum concentration of methanol in the reaction zone.

The flow rate of the overhead liquid product was increased to 2.5 cc/min in the EXAMPLES 5A and 5B. Methyl carbamate solutions were pumped into the reboiler of the distillation still during the run to simulate the continuous operation. When the reaction was carried out as at the high flow rate there was little improvement compared with lower flow rate (1.5 cc/m in EXAMPLE 3A, Table 2). The increased overhead rate simply diluted the concentration of dimethyl carbonate from 16–18% in the EXAMPLE 3A to about 9%, which is undesirable for the separation of dimethyl carbonate from the overhead liquid product. When the reaction was carried out in the absence of triglyme solvent (EXAMPLE 5B), the concentration of dimethyl carbonate in the overhead product was nearly doubled with improved apparent selectivity of dimethyl carbonate and the production of much less methylamine than in the EXAMPLE 3B, although little change in N-MMC formation was noticed. The concentration of dimethyl carbonate in the overhead liquid product was only about half of the EXAMPLE 5A, resulting in about ⅓ less removal of dimethyl carbonate as the overhead liquid product compared with the EXAMPLE 5A as shown in Table 1. Although the concentration of urea in the bottom products is not known, the conversion of methyl carbamate appears to be higher for the EXAMPLE 5A than 5B due to effective removal of both dimethyl carbonate and ammonia from the reaction zone.

TABLE 2

|  | Example | |
| --- | --- | --- |
| Solvent in reboiler | 5A<br>100 MeOH-100 Triglyme | 5B<br>200 MeOH |
| Reboiler Temp, ° F. | 355 | 355 |
| Ovhd P, psig | | |
| initial | 39.4 | 207.7 |
| final | 123.9 | 299.5 |
| Ovhd Prod Rate, cc/min | 2.5 | 2.5 |
| Mass Balance, % | 96.1 | 98.7 |
| Mole Balance*, % | 88.9 | 87.5 |
| App. MC Conv*, % | 82.9 | 67.6 |
| App. Selectivity*, m % | | |
| DMC | 88.7 | 72.2 |
| N-MMC | 0.9 | 8.4 |
| DMC recovered as Ovhd Prod, g | 169.7 | 108.3 |

*The urea content in the reboiler was not included in the calculation.

EXAMPLE 6A

Figure 5:
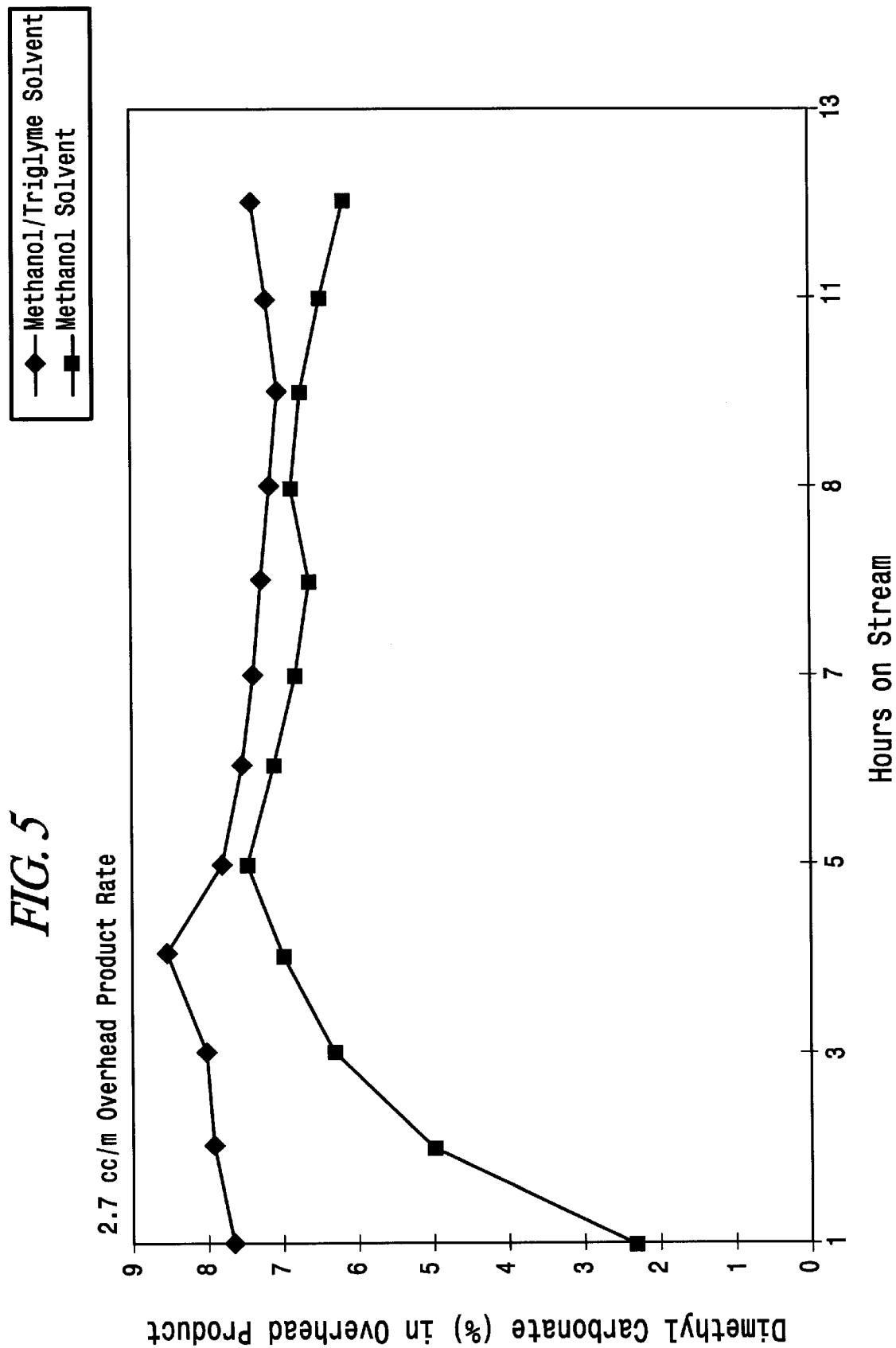
FIG. 5 is a plot of dimethyl carbonate in overhead versus hours on stream comparing methanol only with methanol+ triglyme at a 2.7 cc/min overhead rate.

The reboiler of the distillation still was charged with 125 g methyl carbamate, 100 g methanol, 100 g triglyme and 24.8 g dibutyltin dimethoxide. The reboiler temperature was maintained at 353–357° F. by controlling the overhead pressure during the reaction. The flow rate of the overhead liquid product was set at 2.7 cc/min. A urea solution prepared by dissolving 105.6 g urea in 2200 g methanol was pumped into the reboiler to maintain a constant liquid level in the reboiler. The reaction was terminated after 12 hours uninterrupted continuous operation. The result of this experiment is listed in Table 3. The change in the composition of dimethyl carbonate in the overhead products during the run is illustrated in FIG. 5. The overhead pressures at the beginning and the end were 47.9 psig and 49 psig respectively. The column temperatures at the bottom and top section of the column were 231° F. and 219° F. at the beginning and 232° F. and 200°respect the end of 12 hours run respectively. While the analysis of the sample taken from the reboiler at the end of 12 hours run indicated 1.1% dimethyl carbonate, 13.1% methanol, 30.2% methyl carbamate, 0.8% N-MMC, 54.3% triglyme and 0.5% unknown, the overhead product contained 7.3% dimethyl carbonate and no methylamine. All the overhead samples taken during the 12 hours run contained no detectable amount of methylamine. The content of urea in the bottom product sample was unknown because urea could not be analyzed by gas chromatography due to urea decomposition.

EXAMPLE 6B

The reaction was carried out by utilizing the distillation still disclosed herein as in Example 6A but without the cocatalyst. The reboiler of the distillation still was charged with 125 g methyl carbamate, 200 g methanol, and 25.6 g dibutyltin dimethoxide. The reboiler temperature was maintained at 352–356° F. by controlling the overhead pressure during the reaction. The flow rate of the overhead liquid product was set at 2.7 cc/min. A urea solution prepared by dissolving 105.6 g urea in 2000 g methanol was pumped into the reboiler to maintain the constant liquid level in the reboiler. The reaction was terminated after 12 hours uninterrupted continuous operation. The result of this experiment is listed in Table 3. The change in the composition of dimethyl carbonate in the overhead product during the run is illustrated in FIG. 5. The overhead pressures at the beginning and the end were 222 psig and 236.7 psig, respectively. The column temperatures at the bottom and top section of the column were 332° F. and 311° F. at the beginning and 326° F. and 314° F. at the end of 12 hours run. While the analysis of the sample taken from the reboiler at the end of 12 hours run indicates 8.2% dimethyl carbonate, 45.3% methanol, 37.3% methyl carbamate, 8.0% N-MMC, and 0.8% unknown, the overhead samples taken during the first 6 hours run contained no detectable amount of methylamine. The overhead samples during the second 6 hours run contained 0.08 to 0.1% methylamine. The content of urea in the bottom product sample was unknown because urea could not be analyzed by gas chromatography due to urea decomposition.

TABLE 3

|  | Example | |
| --- | --- | --- |
| Solvent | 6A<br>100 MeOh-100 Triglylme | 6B<br>200 MeOH |
| Reboiler Temp, ° F. | 355 | 355 |
| Ovhd P, psig | | |
| Initial | 47.9 | 222 |
| Final | 49 | 236.7 |

TABLE 3-continued

|  | Example | |
| --- | --- | --- |
|  | 6A | 6B |
| Solvent | 100 MeOh-100 Triglylme | 200 MeOH |
| Ovhd Prod Rate, cc/min | 2.7 | 2.7 |
| Mass Balance, % | 95.9 | 96.5 |
| DMC produced (m %)* | 53.6 | 49.4 |
| N-MMC produced (m %)* | 0.5 | 5.8 |
| Methylamine (%) in ovhd | 0 | 0–0.1 |
| DMC recovered as Ovhd Prod, g | 153.5 | 129.3 |

*Calculated based on the combined total methyl carbamate and urea charged into the reboiler during the run.

The EXAMPLE 6A simulates the continuous run for which an urea solution is pumped into the reboiler (reactor) of the distillation still to convert urea to dimethyl carbonate. The experiments demonstrate that urea can be converted to dimethyl carbonate in one step, that is, it is not necessary to convert urea to methyl carbamate in one reactor and then convert methyl carbamate to dimethyl carbonate in another reactor because the extra amount of ammonia produced by the Reaction 1 can effectively be removed from the reaction zone (reboiler), when urea is converted to methyl carbamate although one may choose to produce dimethyl carbonate in two steps. As shown in Table 3, when the reaction was carried out according to the preferred embodiment, a superior result was obtained again; higher productivity of dimethyl carbonate and lower formation of by-products. When triglyme was not used as cocatalyst as well as solvent the amount of N-MMC produced is 10 times higher than the reaction carried out according to the present invention.

Since, to convert urea to methyl carbamate (Reaction 1), urea has to react with methanol, that is, methyl carbamate has to compete with urea for methanol to produce dimethyl carbonate (Reaction 2). The analysis of bottom product taken after 12 hours run indicates that the methanol concentration in the EXAMPLE 1A (with cocatalyst) appears to be too low (13.1%) for Reaction 1 and Reaction 2 to occur consecutively without competition for methanol. The amount of triglyme in the reboiler of the distillation still was too high at the start of the run indicating that when an urea solution is pumped into the reboiler to produce dimethyl carbonate in a single step the ratio of triglyme to methanol used to convert methyl carbamate to dimethyl carbonate should be readjusted, e.g., lowered.

EXAMPLE 7

This example illustrates the actual production of DMC by one step.

Figure 6:
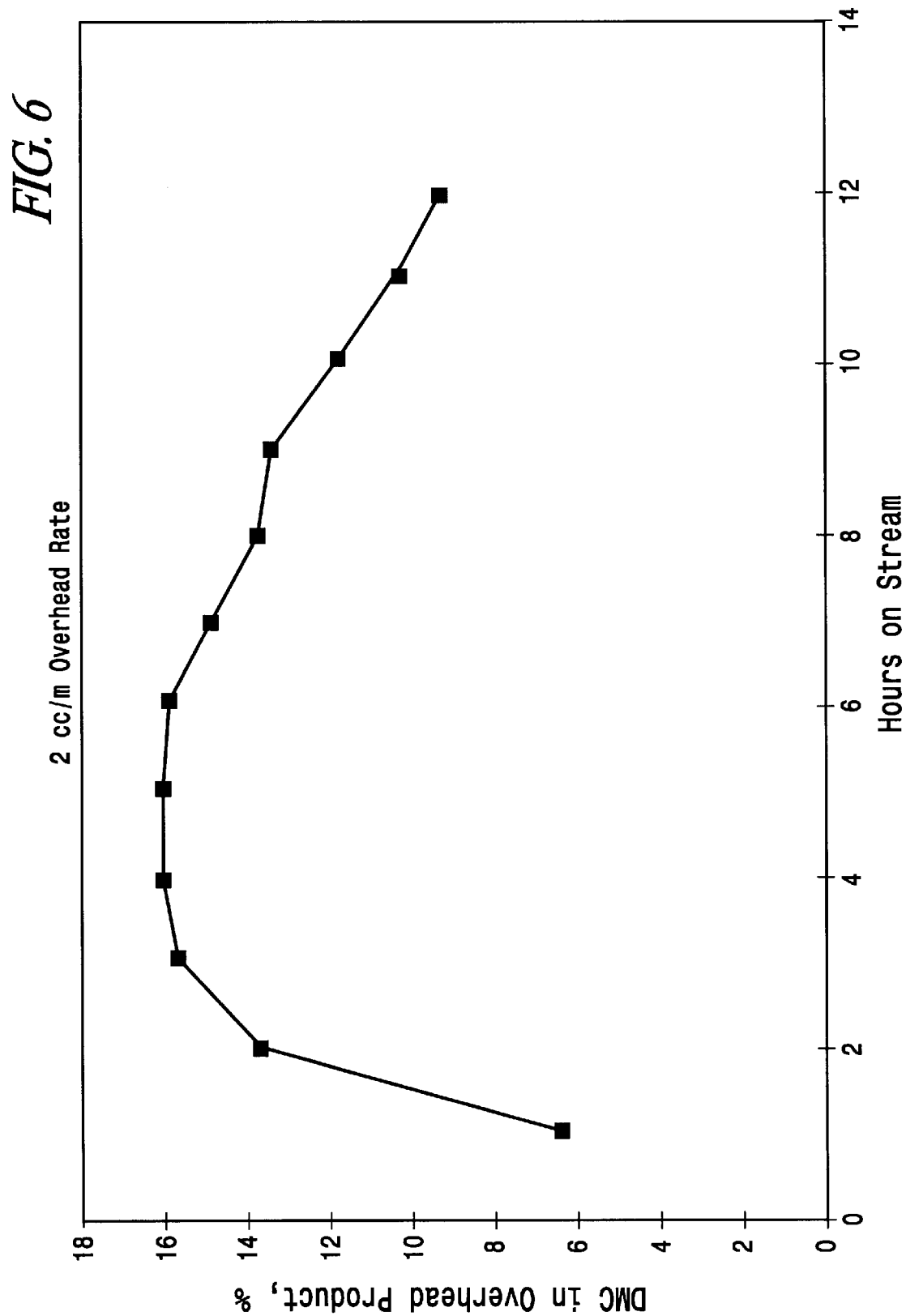
FIG. 6 is a plot of dimethyl carbonate in overhead versus hours on stream for a single step process.

The reboiler of the distillation still was charged with 125 g methyl carbamate, 120 g methanol, 80 g triglyme and 25 g dibutylin dimethoxide. The reboiler temperature was maintained at 349–357° F. by controlling the overhead pressure during the 12 hours uninterrupted run. The flow rate of the overhead liquid product was set at 2 cc/min. A urea solution prepared by dissolving 105.6 g urea in 2200 g methanol was pumped into the reboiler to maintain a constant liquid level in the reboiler. The reaction was terminated after 12 hours uninterrupted operation. The result of this experiment is listed in Table 4. The change of the DMC composition in the overhead products is shown in FIG. 6. The overhead pressures at the beginning and the end of 12 hours run were 66 and 134.7 psig, respectively. The column temperatures at the bottom and top section of the column were 248° F. and 233° F. at the beginning, and 286° F. and 274° F. at the end of 12 hours, respectively. While the analysis of the sample taken from the reboiler a the end of 12 hours run indicated 3.8% dimethyl carbonate, 20.9% methanol, 21.1% methyl carbamate, 1.5% N-MMC, 52.0% triglyme, 0.2% unknown, 0.2% methylamine (or water) and 0.3% ammonia, the overhead product contained 9.0% dimethyl carbonate, 88.4% methanol, 0.1% methylamine (or water) and 2.5% ammonia. The content of urea in the bottom product sample was unknown because urea could not be analyzed by gc due to urea decomposition. The unit was shut down for the next day's run. The weight of the composite overhead product was 1054 g and the weight of the urea solution pumped into the reboiler was 1252 g. The total samples taken out from the unit was 210.8 g. There was lower liquid level in the reboiler from 8 to 12 hours on stream. The composite overhead product contained 11.5% dimethyl carbonate. A vent gas was collected for 12 hours during the reaction (very little gas volume) and the analysis of this vent gas indicated 0.05 vol % $CO_2$ and 2.1 vol $O_2$ indicating very little decomposition of methyl carbamate or urea.

The run was continued the next day by pumping a mixed solution prepared by mixing 1650 g methanol with 142.5 g triglyme into the reboiler. The reboiler temperature was maintained at 348–359° F. by controlling the overhead pressure. The flow rate of the overhead liquid product was set a 2 cc/min. The reaction was terminated after 10 hours uninterrupted operation. The result of this experiment is listed in Table 4. The overhead pressures at the beginning and the end of 10 hours uninterrupted run were 232.1 and 201.7 psig, respectively. The column temperatures at the bottom and top section of the column were 248° F. and 233° F. at the beginning, and 322° F. and 313° F. at the end of 10 hours run, respectively. While the analysis of the sample taken from the reboiler at the end of 10 hours (total 22 hours from the very beginning) run indicated 1.7% dimethyl carbonate, 22.2% methanol, 1.5% methyl carbamate, 1.3% N-MMC, 71.9% triglyme, 1.3% unknowns and 0.1% air, the overhead product contained 3.8% dimethyl carbonate, 94.94% methanol and 1.2% ammonia. The content of urea in the bottom product sample was unknown, because urea could not be analyzed by gc due to urea decomposition. The weight of the composite overhead product was 956 g and the weight of the mixed solution pumped into the reboiler was 1088. The total weight of the samples taken out from the unit was 197.2 g. The total weight of the inventory material collected from the column and the reboiler was 249. The vent gas was collected during the run (very small gas volume) and it contained 10.0 vol % $CO_2$ and 0.7 vol $O_2$. The change of DMC composition in the overhead product for the second portion of the run is included in FIG. 6. High DMC concentration in the overhead product is very desirable because the DMC separation is a costly process due to the formation of binary azeotrope with methanol. As shown in Table 4 the DMC selectivity is excellent (98.2%). When the urea solution is pumped directly into the reboiler in the one step synthesis process, very little methyl carbamate decomposes resulting in the best selectivity so far.

TABLE 4

| Solvent | 120 MeOH/80 TG | |
| --- | --- | --- |
| Pump-in Solution | Urea in MeOH(12 hrs) | Meoh/TG(10 hrs) |
| Reboiler Temp, ° F. | 349–357 | 358–359 |
| Ovhd P, psig | | |
| Initial | 66 | 232.1 |
| Final | 134.7 | 201.7 |

TABLE 4-continued

| Solvent | 120 MeOH/80 TG | |
| --- | --- | --- |
| Pump-in Solution | Urea in MeOH(12 hrs) | Meoh/TG(10 hrs) |
| Ovhd Product Rat, cc/m | 2 | 2 |
| Mass Balance, % | | 100.1 |
| Mole Balance*, % | | 99.8 |
| App. Conversion*, % | | 98.3 |
| Selectivity*, % | | |
| DMC | | 98.2 |
| N-MMC | | 1.6 |
| DMC Recovered as Ovhd Product, g | 151.3[1] | 209.1[2] |

App.; apparent
*Calculated based on combined methyl carbamate and urea consumed during the reaction, assuming no uncovered urea left in the reactor at the end of run.
[1]For the first 12 hours run.
[2]For the total 22 hours run.

The invention claimed is:

1. A homogeneous catalyst useful for reacting urea and primary alcohols to produce dialkyl carbonates comprising a complex of an organotin compound with a high boiling electron donor atom compound comprising bidentate ligand which form 1:1 bidentate and/or 1:2 monodentate adducts with $R'_2SnX_2$ (X=Cl, R'O, R'COO or R'COS), $R'_3SnX$, $R'_2SnO$, $Ph_{3-n}R'SnX_n$ or $Ph_{4-n}SnX_n$ (wherein $R'=C_qH_{2q-1}$ n=0, 1 or 2 and q=2 to 12) and mixtures thereof.

2. The catalyst according to claim 1 wherein said organotin compound comprises dibutyltin dimethoxide.

3. The catalyst according to claim 1 wherein said high boiling electron donor atom compound comprises triethylene glycol dimethyl ether.

4. The catalyst according to claim 1 wherein said organotin compound comprises dibutyltin dimethoxide and said high boiling electron donor atom compound comprises triethylene glycol dimethyl ether.

5. The homogeneous catalyst according to claim 1 wherein said high boiling electron donor atom compound comprises materials having the general formula $RO[CH_2(CH_2)_kCH_2O]_mR$, wherein each R is independently selected from $C_{1-12}$ alkyl, alkaryl or aralkyl moieties, k=0, 1, 2 or 3 and m=1, 2, 3, 4 or 5 and mixtures thereof.

6. The homogeneous catalyst according to claim 1 wherein said organotin compound comprises $R'_2SnX_2$.

7. The homogeneous catalyst according to claim 1 wherein said organotin compound comprises $R'_3SnX$.

8. The homogeneous catalyst according to claim 1 wherein said organotin compound comprises $R'_2SnO$.

9. The homogeneous catalyst according to claim 1 wherein said organotin compound comprises $Ph_{3-n}R'SnX_n$.

10. The homogeneous catalyst according to claim 1 wherein said organotin compound comprises $Ph_{4-n}SnX_n$.

11. The homogeneous catalyst according to claim 5 wherein said organotin compound comprises $R'_2SnX_2$.

12. The homogeneous catalyst according to claim 5 wherein said organotin compound comprises $R'_3SnX$.

13. The homogeneous catalyst according to claim 5 wherein said organotin compound comprises $R'_2SnO$.

14. The homogeneous catalyst according to claim 5 wherein said organotin compound comprises $Ph_{3-n}R'SnX_n$.

15. The homogeneous catalyst according to claim 5 wherein said organotin compound comprises $Ph_{4-n}SnX_n$.

* * * * *

UNITED STATES PATENT AND TRADEMARK OFFICE
CERTIFICATE OF CORRECTION

PATENT NO.    : 6,010,976
DATED         : January 4, 2000
INVENTOR(S)   : J. Yong Ryu It is certified that error appears in the above-identified patent and that said Letters Patent is hereby corrected as shown below:

Abstract:
Line 6, change "q = 2" to read -- q = 1 --

Column 2,
Line 35-36, change the formula to RO

Signed and Sealed this

Ninth Day of October, 2001

Attest:

NICHOLAS P. GODICI
Attesting Officer    Acting Director of the United States Patent and Trademark Office

UNITED STATES PATENT AND TRADEMARK OFFICE
CERTIFICATE OF CORRECTION

PATENT NO. : 6,010,976
DATED : January 4, 2000
INVENTOR(S) : J. Yong Ryu

It is certified that error appears in the above-identified patent and that said Letters Patent is hereby corrected as shown below:

<u>Title page,</u>
Item [57], ABSTRACT,
Line 6, the equation "$R'=C_qH_{2q-1}$" should read -- $R'=C_qH_{2q+1}$ --

<u>Column 3,</u>
Line 31, the equation "$R'=C_qH_{2q-1}$" should read -- $R'=C_qH_{2q+1}$ --

<u>Column 17,</u>
Line 27, the equation "$R'=C_qH_{2q-1}$" should read -- $R'=C_qH_{2q+1}$ --

Signed and Sealed this

Thirtieth Day of July, 2002

*Attest:*

*Attesting Officer*

JAMES E. ROGAN
*Director of the United States Patent and Trademark Office*